(12) United States Patent
Kuppuswamy et al.

(10) Patent No.: US 10,092,640 B2
(45) Date of Patent: Oct. 9, 2018

(54) COMBINATION HEPTAVALENT VACCINE

(75) Inventors: Gopinathan Kuppuswamy, Hyderabad (IN); Vijayanand Thiagarajan, Hyderabad (IN)

(73) Assignee: Bharat Biotech International Limited, Hyderabad (IN)

( * ) Notice: Subject to any disclaimer, the term of this patent is extended or adjusted under 35 U.S.C. 154(b) by 0 days.

(21) Appl. No.: 13/978,397

(22) PCT Filed: Jan. 3, 2012

(86) PCT No.: PCT/IN2012/000005
§ 371 (c)(1),
(2), (4) Date: Jul. 4, 2013

(87) PCT Pub. No.: WO2012/093406
PCT Pub. Date: Jul. 12, 2012

(65) Prior Publication Data
US 2013/0280293 A1    Oct. 24, 2013

(30) Foreign Application Priority Data
Jan. 5, 2011   (IN) .............................. 27/CHE/2011

(51) Int. Cl.
| | | |
|---|---|---|
| A61K 39/00 | (2006.01) | |
| C07K 16/28 | (2006.01) | |
| A61K 39/395 | (2006.01) | |
| C07K 14/705 | (2006.01) | |
| A01N 1/02 | (2006.01) | |
| A61K 39/295 | (2006.01) | |
| A61K 39/04 | (2006.01) | |
| A61K 39/08 | (2006.01) | |
| A61K 39/102 | (2006.01) | |
| A61K 39/05 | (2006.01) | |
| A61K 39/02 | (2006.01) | |
| A61K 39/12 | (2006.01) | |

(52) U.S. Cl.
CPC ............ *A61K 39/295* (2013.01); *A61K 39/04* (2013.01); *A61K 39/05* (2013.01); *A61K 39/08* (2013.01); *A61K 39/099* (2013.01); *A61K 39/102* (2013.01); *A61K 39/12* (2013.01); *A61K 2039/5252* (2013.01); *A61K 2039/55505* (2013.01); *A61K 2039/6037* (2013.01); *C12N 2720/12334* (2013.01); *C12N 2730/10134* (2013.01); *C12N 2770/32634* (2013.01); *Y02A 50/466* (2018.01)

(58) Field of Classification Search
CPC ......... G01N 33/6863; G01N 2333/715; C07K 14/7158; C12N 9/6489; C12Q 1/6883
See application file for complete search history.

(56) References Cited

FOREIGN PATENT DOCUMENTS

| WO | WO2007007344 | * | 1/2007 |
|---|---|---|---|
| WO | WO 2010/046935 | | 4/2010 |
| WO | WO2010046935 | * | 4/2010 |

OTHER PUBLICATIONS

Kaufmann et al., "Challenges and responses in human vaccine development", Current Opinon in Immunolgoy, 2014, 28:18-26.*
Kang et al., "Rotavirus Vaccines", 2006, Indian Journal of Medical Microbiology, 24(4):252-257.*
Kang, "Rotavirus vaccines" Indian J Med Microbiol 2006;24:252-7.
Ward, et al, "Why does the world need another rotavirus vaccine?" Ther. Clin. Risk Manag. Feb. 2008; 4(1): 49-63.
Papaevangelou "Current combined vaccines with hepatitis B" Vaccine, 1998 Elsevier Ltd, GB, vol. 16,Nr:Suppl,pp. S69-S72.
Vesikari, et al. "Immunogenicity and safety of the human rotavirus vaccine Rotarix(TM) co-administered with routine infant vaccines following the vaccination schedules in Europe" Vaccine, 2010, Elsevier; vol. 28,Nr:32,pp. 5272-5279.
International Search Report from the European Patent Office, dated Apr. 6, 2012, issued in connection with corresponding International Application No. PCT/IN2012/000005.

* cited by examiner

*Primary Examiner* — Barry A Chestnut
(74) *Attorney, Agent, or Firm* — Remenick PLLC

(57) ABSTRACT

The invention provides a stable immunogenic composition for prevention and prophylaxis of infections caused by rota virus, poliomyelitis virus, *Haemophilius influenza*, Hepatitis B, *Corynebacterium diphtheriae, Clostridium tetani, Bordatella pertusis* (acellular) in a single combined vaccine. The invention also provides for a bivalent immunogenic composition against rota virus and polio virus. The process of making such compositions of the multivalent antigens are also disclosed. The present invention also relates to the production and use of such vaccines for prophylaxis against the infections mentioned above.

15 Claims, No Drawings

COMBINATION HEPTAVALENT VACCINE

This application is national phase application under 35 U.S.C. § 371 of International Application No. PCT/IN2012/000005, filed Jan. 3, 2012, which claimed priority to 27/CHE/2011, filed on Jan. 5, 2011; the disclosures of which are all hereby incorporated reference herein.

FIELD OF THE INVENTION

The invention relates to stable immunogenic combination vaccine for prophylaxis and treatment against any genotypes or antigenic variants of rotavirus, poliomyelitis, pertussis, Hepatitis B, *Haemophilus influenzae*, diphtheria and tetanus infections. More particularly, the invention relates to stable immunogenic combination vaccine for prophylaxis and treatment against any genotypes or antigenic variants of rotavirus, poliomyelitis, pertussis, Hepatitis B, *Haemophilus influenzae*, diphtheria and tetanus infections, wherein any of the each component individual antigens is not impaired by the presence of other component antigens, thereby conferring an antibody titer equivalent or superior to the criterion for the seroprotection for each antigenic component. The invention also provides for a bivalent vaccine composition for immunizing infants against rotavirus and poliomyelitis infections.

BACKGROUND OF THE INVENTION

Vaccination is an important tool for handling health care programs both in developed and developing nations. The number of recommended vaccines has increased significantly in recent years against individual infections. The schedule of infants and children may require more than 24-25 separate shots of vaccines for effective immunization against life threatening diseases, as of now.

A combination vaccine which can provide immunogenicity against large number of diseases is always advantageous over the monovalent vaccines. We cannot reduce the number of immunizations required in infants and children to protect them from various fatal diseases but the compliance can be increased by reducing the number of separate vaccinations. A combination vaccine is advantageous over monovalent vaccine as it not only increases the compliance but it is also cost effective and convenient thereby reducing the chances of missing any vaccination shot. However, due to complications associated with the preparation of such combination vaccines like stability of such combination vaccines due to possible interaction between the antigens has always been a challenge before the scientist community.

Hence, the current global scenario calls for a more-effective, acceptable, cost effective and reliable method for immunization against many fatal diseases. The availability of combination vaccines containing protective antigens against majority of diseases, for which universal immunization is recommended in infancy, helps in simplifying the implementation, increasing the acceptance, reducing the global cost of immunization programs and improving disease control. Therefore, cost, convenience and compliance factors contribute to enhanced use of combination vaccines over monovalent vaccines. It can also increase the hand-to-reach patients or populations or frequent non-attendees (Rumke, 1994).

The development of multivalent vaccine capable of protecting against diphtheria (D), tetanus (T), pertussis (P), poliomyelitis, hepatitis B and *Haemophilus influenzae* type b (Hib) has been an evolutionary process which started in the 1950s when diphtheria and tetanus toxoids were first multivalent with inactivated whole cell pertussis(wP) vaccine (Mallet et al; 2004). Use of detoxified and inactivated pertusis toxin and filamentous hemagluttinin (PT+FHA) as acellullar pertusis vaccine components has been described in Robinson, A., Gorrige, A. R., Funnell, S. G. P., and Fernandez, M. (1989). *Serospecific protection of mice against in infection with Bordetella pertussis*. Vaccine 7: 321-324. Vaccines combining diphtheria-tetanus-pertussis antigens are available and widely used for over 60 yrs. Expanded quadrivalent and pentavalent combination vaccines also have been developed that include *Haemophilus influenzae* type b vaccine. Pentavalent combinations that include DPT-Hib-Hepatitis B (HB) are used in several developed and developing countries.

Some of the multiple component vaccines commercially available till date are mentioned as under.

Tripedia® by Sanofi Pasteur is a diphtheria, tetanus, and acellular pertussis (whooping cough) (DaPT) vaccine. It is approved by FDA for use in infants and children under the age of seven. It is also approved to be mixed together with ActHIB®, a *Haemophilus influenzae* type b vaccine (Hib vaccine), for children 15 to 18 months of age (Trihibit®).

Daptacel® also by Sanofi Pasteur is a diptheria and tetanus toxoids and acellular pertussis vaccine adsorbed (DaPT), approved for routine immunization in infants and children six weeks through six years of age. It is administered via intramuscular injection in four consecutive doses of the five dose immunization series. The four doses are given at approximately two months, four months, six months and six months after the third dose.

A vaccine Kinrix® for DaPT-Inactivated Polio Virus (IPV) has been marketed outside the United States since 1996 which is equivalent to getting the DTaP and IPV vaccines as separate shots with the MMR booster at the 4 to 6 years age of a child.

Pentavalent vaccines to mention are Pediarix® [Diphtheria and Tetanus Toxoids and Acellular Pertussis adsorbed, Hepatitis B (Recombinant) and Inactivated Poliovirus Vaccine Combined] and Pentacel® a DTaP-IPV/Hib vaccine that has been used since 1997 as combined vaccine shots to be administered to children as a four dose series, with the primary doses at two, four, and six months, and a booster dose at 15 to 18 months.

Infanrix® hexa by GlaxoSmithKilne, administered intramuscularly, is a diphtheria, tetanus, acellular pertussis, hepatitis B (HB), inactivated poliomyelitis and *Haemophilus influenzae* type b (Hib) conjugate vaccine, indicated for primary and booster vaccination of infants. Infanrix hexa should be administered as a two- or three-dose primary vaccination course in infants aged less than or equal to 6 months, followed by booster vaccination between 11 and 18 months of age, with an interval of at least 6 months between the last dose of primary vaccination and the booster dose. A detailed study on Immunogenicity and safety of a new liquid hexavalent combined vaccine compared with separate administration of reference licensed vaccines in infants was published by Mallet E, Fabre P, Pines E, et al. *Pediatr Infect Dis J* 2000; 19:1119-27. Thus, Hexavalent vaccines have been used in several European countries as well as in US which can provide immunization only against six important childhood diseases with single injection. It is desirable that a combination vaccine must include further antigens than hexavalent antigens so that a single vaccination may include immunization against other serious diseases for example rotavirus.

Rotavirus is the leading cause of severe diarrhea disease in infants and young children worldwide. About 600000 children die every year from rotavirus infection, with more than 80% of all rotavirus related deaths occurring in resource poor countries in south Asia and sub-Saharan Africa. The present invention teaches a novel combination of D-aP-T-Hib-HepB-IPV and inactivated rotavirus antigens (IRV) in a stable heptavalent combination vaccine composition.

All rotavirus vaccines that have entered clinical trials in children have been live oral strains and several of these have proven effective and become licensed. However, none of these vaccines have been tested in the target population in poor countries of Africa and Asia where rotavirus remains a prime killer of children. However substantial setback for the oral live vaccine cause adverse events like intussception and the rotaviruses exhibit enormous diversity (Human vaccines 4:3, 143-147:2008). In the present invention we have also pursued an alternative strategy to develop inactivated rotavirus vaccine (IRV) and this rota antigen as part of a combination childhood vaccine with combined sabin type I, II, and III antigen as a novel divalent combination vaccine. The cell line used for the propagation of the rotavirus is vero cells, because this cells have a broad sensitivity to various types of viruses and widely used in human viral vaccine production. Rotavirus vaccines are not available in the prior art as injectable vaccine still now. All rotavirus vaccines available are administered orally. Therefore, it is desirable to include a rotavirus antigen that would confer immunity against any strains of rotavirus in an injectable form in combination with other antigens.

WO1993/024148 discloses an invention of multivalent vaccine containing antigens IPV-DPT-Hib-Hepatitis B wherein DTP is adsorbed to Aluminium Hydroxide or Aluminium Phosphate and Hib is adsorbed to only Aluminium Phosphate, wherein the Hib antigen is used extemporaneously by mixing to the other antigens just prior to the administration. WO1997/00697 discloses a DPT-Hib and pertusis multivalent vaccine adsorbed to aluminium phosphate, in which one container has a freeze-dried vaccine and the other container comprises a second antigen.

WO1998/000167 discloses a D-T-aP-IPV-Hib antigen vaccine and WO1999/13906 describes a multiple component vaccine in which certain components may be reconstituted from a lyophilized state by the other components of the vaccine, or may exist in a single solution, and administers the vaccine in a specially designed container at the time when the vaccination is performed.

WO2000/07623 describes a multi-component vaccine composition having acellular pertussis vaccine components (PT and FHA), diphtheria toxoid (DT), tetanus toxoid (TT), a conjugate of a capsular polysaccharide of (*Haemophilus influenze*) type b and tetanus toxoid or diphtheria toxoid (Hib), Hepatitis B Surface Ag (HBsAg) and inactivated poliovirus (IPV) which may be in a single solution, or certain components may be reconstituted from a lyophilized state by the other components of the vaccine. WO2002/000249 discloses a capsular polysaccharide of *H. influenza* b not adsorbed onto an aluminium adjuvant salt, and two or more further bacterial polysaccharides which may include whole cell pertussis, tetanus toxoid, diphtheria toxoid, Hepatitis B surface antigen (HbsAg), and/or conjugate polysaccharides of *N. meningitides* type A, or B, or C as antigens in a single quadrivalent and/or trivalent vaccine. WO2006/097851 discloses a multivalent vaccine which can be prepared extemporaneously at the time of use by mixing together two components the first component comprising D, T, wP and HBsAg antigens and a second component comprising a Hib conjugate and one or more meningococcal conjugates. WO2007/054820 relates to a vaccine composition wherein the D, T, and aP antigens are specifically adsorbed on aluminum hydroxide and the Hib and the Hep B antigens are adsorbed onto aluminium phosphate which do not exist in a fully liquid stable composition.

U.S. Pat. No. 6,333,036 talks about a multivalent vaccine which uses Hib conjugate polysaccharide polyribosylribitol phosphate (PRP) adsorbed to aluminium phosphate including D,T, and aP antigens. The Hep B antigen is adsorbed to aluminum hydroxide and the same is not a fully liquid composition to form a multivalent vaccine.

European Patent 1028750 teaches a multivalent vaccine which has the D, T, aP adsorbed to aluminium phosphate and the Hep B antigen not being adsorbed to aluminium hydroxide and also does not exist in a single stable liquid composition to form a combined vaccine.

Although the eradication of poliomyelitis from the western world, and its global decline, is a result of successful use of oral polio vaccine (OPV) in most parts of the world (Plotkin, 1995), the potential risk of vaccine associated paralytic poliomyelitis (VAPP) with OPV, has led many countries to switch over to using IPV for routine immunization. Some other prior art publications in the field are Plotkin SA. Inactivated poliomyelitis vaccine for the United States: a missed vaccination opportunity. *Pediatr Infect Dis J* 1995; 14:835-9 and Rümke HC. Are different combined vaccines needed in different parts of Europe? A point of view from a Northern European country. *Biologicals* 1994; 22:425-7. All the patent applications detailed above have different adjuvant to different antigens, and is not present as a single liquid composition in a single vial.

WO2008/044611 discloses a method for the preparation of a mixed IPV-DPT vaccine comprising an inactivated poliovirus Sabin strains type I, II, and III grown in Vero cells, a protective antigen against *Bordetella pertussis*, a diphtheria toxoid and a tetanus toxoid, which involves the step of producing a poliovirus Sabin strain having a high titer.

All the patent applications mentioned above require reconstitution of the individual components prior to administration of the vaccine. They may not be called combined in the literary sense of the term yet, may be called as a multivalent vaccines to confer immunity against at the maximum of six antigens. The mixing of antigenic components prior to administration from different vials results in diminishing of the antibody titer against any particular antigen owing to interference of antigenic interactions. US publication 2011/0206726A1 teaches a fully liquid hexavalent combination vaccine comprising D-T-aP-IPV, -Hep B and Hib antigens wherein Hib is not substantially adsorbed to any adjuvant and D-T-aP adsorbed to aluminum hydroxide and Hep B adsorbed to aluminium phosphate in a single vial. It also specifies that, antigenic competition in such multivalent vaccines often results in a diminished response to certain individual antigens. The patent application recognizes an inherent problem of mixing of lyophilized vaccines with liquid vaccines which represents supplementary constraint for the practitioner and involves a possibility of the same being carried out badly. It also recognizes that the usage of multi-compartment syringes having separate chambers for liquid and lyophilized vaccines is too difficult to execute and no reduction in production costs of the vaccine is possible, thereby no reduction in the cost of immunization also. Although this application describes a liquid combination vaccine in a single vial, it does not describe a combined vaccine composition containing as much as 7 different antigens. It does not talk about conferring protection or immunity to infections caused by rotavirus in the combined vaccine composition.

Hence, in this invention, it has been made possible to develop such a combination heptavalent vaccine which could be able to provide protection against poliovirus, rotavirus, *Haemophilus influenzae*, Hepatitis B, Diptheria, Tetanus and acellullar Pertussis by administration using a single combined vaccine. The present invention overcomes the limitations of the prior art by providing a stable, combination heptavalent vaccine (Inactivated poliovirus (Sabin)—Inactivated rotavirus—*Haemophilus influenzae* type b—Hepatitis B surface antigen—Diptheria-Tetanus-Pertussis(aP)) which permits vaccination against poliomyelitis, rotavirus, Hib, hepatitis B, diphtheria, tetanus and pertussis by single injection which is stable and fulfills the cirteria of effective seroprotection against each of the antigens with minimal or least antigenic interference in the combined vaccine.

OBJECT OF THE INVENTION

Primary object of the invention is to provide a combination heptavalent vaccine which induces immunogenicity in human beings against at least seven diseases.

Another object of the invention is to provide a fully stable, combination heptavalent vaccine which permits vaccination against poliomyelitis, rotavirus, Hib, hepatitis B, diphtheria, tetanus and pertussis by single injection.

Another object of the invention is to provide a stable, combination heptavalent (IPV-IRV-Hib-HBsAg-DPT) vaccine comprising Inactivated poliovirus (Sabin type I, II, III), Inactivated rotavirus, strain 116E, *Haemophilus influenzae* type b, Hepatitis B surface antigen, Diphtheria, Tetanus and Pertussis (aP)) antigens in one single combined vaccine.

A further object of the invention is to provide a method for preparation of combination heptavalent Inactivated poliovirus (Sabin type I, II, III)—Inactivated rotavirus-Haemophilus influenzae type b—Hepatitis B surface antigen (HBsAg)—Diptheria-Tetanus-Pertussis(aP) vaccine.

Yet another object of the invention is to provide a bivalent Inactivated Polio Virus—Inactivated Rotavirus novel combination vaccine to prevent and treatment of rotavirus and poliomyelitis infections in children in one single combined vaccine.

A further object of the invention is to provide a method for preparation of combination bivalent vaccine.

SUMMARY OF THE INVENTION

Accordingly, present invention provides a stable immunogenic combination vaccine for prophylaxis and treatment against any genotypes or antigenic variants of rotavirus, poliomyelitis, pertussis, Hepatitis B, *Haemophilus influenzae*, diphtheria and tetanus infections, wherein any of the each component individual antigens is not impaired by the presence of other component antigens, thereby conferring an antibody titer equivalent or superior to the criterion for the seroprotection for each antigenic component.

The combination vaccine of the invention comprises a mixture of antigens for protection against diseases such as diphtheria, tetanus, pertusis, and infections caused by *Haemophillus influenzae*, Hepatitis B, polio viruses and rotaviruses. The invention in particular relates to a novel fully liquid stable heptavalent vaccine composition adsorbed to Aluminium phosphate comprising:

i) Three types of inactivated polio virus (type-1,2,3),
ii) Single strain inactivated rotavirus (116E), adsorbed
iii) A conjugate *Haemophilus influenza* type b PRP conjugate to TT
iv) Recombinant Hepatitis B vaccine, adsorbed
v) Diphtheria toxoid (DT), adsorbed
vi) Tetanus toxoid (TT), adsorbed
vii) *Bordetella Pertussis*, acellular(aP) adsorbed The combination heptavalent vaccine of the invention decreases the number of injections required for immunization, improves parental and child satisfaction, decreases pain, is more convenient, improves compliance with one-time immunization, improves record keeping and is more cost effective.

A novel combination vaccine of inactivated sabin I, II, & III and inactivated rotavirus antigens and a process to manufacture the same is also provided. The invention process includes addition of suitable stabilizer during inactivation process of polio and rotavirus.

Further, a method to immunize children against the above mentioned diseases is also provided by injecting all the seven and/or IPV-IRV antigens in a single liquid composition in one vaccine shot. The present invention is further directed towards a combination vaccine that comprises a plurality of the vaccine components that are suitable for the prevention, amelioration and treatment of multiple disease states that meet the criterion for the seroprotection for each of the said vaccine components with least antigenic interference.

DETAILED DESCRIPTION OF THE INVENTION

Detailed embodiments of the present invention are disclosed herein however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

Various antigens used in the heptavalent vaccine of the invention along with a brief description of method of their preparation would now be described in the following paragraphs along with their advantages and applications over the prior art.

i) Inactivated Polio Vaccine

Polioviruses (family picrnaviridae, genus enterovirus) are non-enveloped positive strand RNA virus and are the causative agent for paralytic poliomyelitis. Enterovirus are transient inhabitants of the gastrointestinal tract and are stable at acid pH. Polio viruses have icosahederal capsids consisting of one copy of the RNA genome and 60 copies of each of the viral capsid proteins VP1, VP2, VP3 and VP4.

The virus enters through the mouth and primary multiplication of the virus occurs at the site of implantation in the pharynx and gastrointestinal tract. The incubation period lasts between 3 and 35 days. The infection then enters lymphatic organs by infiltrating monocyte cells in peyers patches. The tonsils, cervical lymph nodes and mesenteric lymph nodes are typical sites for secondary replication. The virus is carried by the bloodstream to various internal organs and regional lymph nodes. Moreover, when the poliovirus affects the medullary respiratory center and death from respiratory paralysis may result.

Two types of polio vaccines are used: oral live polio vaccine and inactivated polio vaccine. The live attenuated oral polio vaccine is highly effective against all three serotypes of polio virus and has been used to interrupted wild type polio virus transmission for the global polio eradication initiative. Oral polio virus strains can effectively induce both humoral and mucosal immunities against polio virus, however they have some inherent disadvantages due to their genetic instability and rapid generation of revertants during virus replication in vaccine recipients. To minimize the potential risk of polio out breaks associated with either circulating vaccine derived polio viruses (cVDPV) and vaccine associated paralytic poliomyelitis (VAPP) strains and to reduce the disease burden related to the use of OPV.

Inactivated polio vaccine (IPV) are mainly produced using the virulent wild type polio virus strains. The probability of wild polio virus escape from IPV production sites to the community which leads to possible risk of outbreak in unimmunized population. In this regards the use of live-attenuated polio virus strains for IPV production instead of the wild-type strains to minimize the risk of poliomyelitis out breaks due to virus release to the community during post-eradication era.

An inactivated polio vaccine which has lost its infectiousness by inactivation of the polio virus inactivated with 0.020 to 0.025% formalin during 2 weeks at 37° C. (*Vaccine* 17, 2059-206:1999). The stability and immunogenicity studies of salk and Sabin-IPV at 37° C. was similar (Biologicals 34, 155-158:2006)

Polio viruses have two different kinds of antigens, namely D-(N) and C—(H) antigens. D antigen is expressed in native virus particles and can induce type specific protective neutralization antibodies in individuals after polio virus infection or vaccination with OPV or IPV. The D antigen can be converted to non-protective C antigen by mild heating, therefore the measurement of D antigen content has been used for the potency test. (*Vaccine* 25, 7041-7046:2007). With respect to immunogenicity in the rat potency test differ significantly. For Type-1 immunogenicity was significantly higher for the sabin in comparison with salk IPV. For type-2, a major reduction in immunogenicity was seen for sabin in comparison with salk IPV. For type 3 a similar immunogenicity was seen for sabin and salk IPV (*Biologicals* 34, 155-158:2006). The present oral live attenuated vaccine strains developed by sabin replicate in the human gut and give rise to viral strains of increased neurovirulence that on very rare occasions, approximately 1 case per 2.5 million doses, causes vaccine associated paralytic poliomyelitis.

Two viral antigens known as D antigens and C antigens are generally present in admixture with in inactivated sabin strain of polio virus. D antigens are complete viral proteins. Antibodies to D antigens have the ability to neutralize the infectious live virus. Therefore, when an inactivated sabin strain of polio virus is to be used as vaccine, the D antigens are required.

There are three types of polio viruses type I, type II and type III each of which causes the disease polio. Therefore when an inactivated sabin strain of poliovirus is used as a vaccine (inactivated polio vaccine), it must have an immunogenicity capable of producing sufficient antibodies to neutralize wild strain of polio virus of each of type I, type II, and type III.

In populations with low vaccine coverage and poor surveillance, vaccine-derived strains can silently circulate for long periods of time leading to poliomyelitis out breaks.

WHO views the exportation of large scale salk-IPV production technology, using wild type polio virus for production into countries with limited resources and/or weak bio-safety regulatory environments where a significant number of population became fully susceptible to polio virus infection following the cessation of OPV use. Therefore, the inactivated polio vaccine IPV in the invention has been developed from live attenuated Sabin strain. In the present specification Sabin strain of polio virus refers to a polio virus strain derived from the attenuated strain of polio virus. Sabin strain polio virus include Sabin type I strain of polio virus, Sabin type III strain of polio virus and Sabin type III strain of polio virus.

Inactivation is nothing but eliminating the infectious ability of the virus using chemicals. The chemical used for inactivating the virus are formaldehyde or beta propiolactone. Polio virus inactivation may be carried out by chemical method. For instance inactivation may be carried out by treating the polio virus with formalin.

ii) Inactivated Rotavirus Vaccine

Rotavirus remains a prime killer of children due to diarrhea, dehydration and malnutrition in countries of Africa and Asian continent. Commercial vaccines have not been tested on target population in these poor countries. The existing live vaccine is not enough to induce immunity and not protecting the complete population. Some time it causes adverse events like intussusceptions also.

When mixed infections with more than one rotavirus strain occurs, the gene segments from the parental viruses may reassort independently due to genetic shift, producing reassortants of mixed parentage, a source of viral diversity.

The present invention provides a novel method for development of inactivated injectable rotavirus vaccine (IRV) antigen in combination with other antigens which overcomes the post vaccination problems associated with the oral rotavirus vaccines known in the art.

The rotavirus strain 116E is a naturally occurring human-bovine ressortant. 116 E is a human rotavirus obtained from asymptomatically infected newborns have p[10]G9 and p[11]G10 antigenic make ups. This live oral vaccine in clinical trial were safe and well tolerated. Penelope H. Denneht: "*Rotavirus vaccines*: an overview," Clinical microbiology Reviews, 198-208 (2008) or BBIL rotavirus patent as example or reference. In the present invention virus inactivation refers to elimination of the infectious ability of a virus. In the two method of inactivation (chemical and physical), most commonly used chemicals are formaldehyde and betapropiolactone. Rotavirus inactivation may be carried out by a method (*Human vaccines: "Immunogenicity of a thermally inactivated rotavirus vaccine in mice* ", 143-147:2008. For instance inactivation may be carried out by treating the rotavirus with heat.

iii) Production of *Bordetella Pertussis* Protective Antigen

The strain used for development and production of acellular pertussis vaccine *Bordetella pertussis* Tohama-I and *Bordetella Bronchiseptica* TY-178.

*Bordetella Pertussis* Tohama-I:

It is gram negative, aerobic, motile, coccobacilli. It produces betahemolysis on Blood agar. It is the one of the strain we are using for isolation and purification of FHA & PRN. Which access major components of acellular pertussis vaccines.

*Bordetella Bronchiseptica* TY-178:

It is gram negative, aerobic, motile, coccobacilli. It producess beta hemolysis on Blood agar. This strain is genetically modified it is used specially for isolation & purification of detoxified PT.

Preparation of Pertussis Toxoid and Filamentous Haemaggulitin

*B.Pertussis* tohama-I/*B.bronchiseptica* TY 178 strain inoculated onto 2 B. G. Agar slants, incubated at 37+0.5° C. for 48 hrs. into incubator. Confluent growth is observed. Then the growth is harvested in to 5 ml normal saline and inoculated into 2×10 ml SS medium at 37+0.50° C. for 24 hrs in shaker incubator at 120 rpm. Growth observed (Stage-I) 5% of stage I culture is transferred to into 2×50 ml of SS medium incubated at 37+0.5° C. for 24 hrs in Shaker incubator at 150 rpm (stage II). Then, stage II culture is transferred to 2×250 ml SS medium incubated at 37+0.5° C. for 24 hrs in shaker incubator at 200 rpm (stage III). Good growth is observed. Purity checked and pool the flask for 5% of seed inoculam for 10 L medium of fermenter according to protocol.

B. P. Tohama-I: Fermenter harvest was collected in a sterile 10 L carbouy and centrifuged at 4200 rpm for 45 min. The collected supernatant which contains FHA antigen, which is filtered by 0.45 um filtration and the cell pellet is processed for Pertactin extraction.

B. Bronchiseptica TY 178: Fermenter harvest was collected in a sterile 10 L carbouy, and centrifuged at 4200 rpm for 45 min. The collected supernatant contains P T antigen filter by 0.45 um filtration. Discard cell pellet after inactivation.

The above 0.45 μm filtered soup which has got FHA and PT is concentrated up to 5-6 folds to its original volume with the help of TFF system followed by diafiltration of the same with phosphate buffer at pH 8.0.

Chromatography-1 (Primary purification):—primary purification is done with the help of Affinity chromatography, and elution's are checked by H A activity for presence of antigen.

Chromatography-2 (Secondary purification):—Secondary purification is done with the help of ion exchange chromatography, and elution's are checked by H A activity for presence of antigen. Purity was checked by SDS PAGE (silver staining).

iv) Diphtheria Toxoid Antigen

Diptheria toxoid antigen was procured from WHO pre-qualified bulk manufacturer. This bulk was used for the preparation of combination vaccine. Combination vaccine was formulated in such a way that each 0.5 ml should contain 25 LF of toxoid.

v) Tetanus Toxoid Antigen

Tetanus toxoid antigen was procured from WHO pre-qualified bulk manufacturer. This bulk was used for the preparation of combination vaccine. Combination vaccine formulated in such a way that each 0.5 ml should contain 7.5 LF of toxoid.

vi) Haemophilus Influenza Type b Conjugate Vaccine

Preparation of *Haemophilus influenza* type b conjugate vaccine involves the following steps:

1. Fermentation of *haemophilus influenzae* type b culture.
2. Extraction and purification of PRP.
3. Activation of PRP with cyanogen bromide and linked with adipic acid dihydrazide.
4. Coupling of purified tetanus toxoid.
5. Purification of conjugate by size exclusion chromatography.

vii) Hepatitis B Surface Antigen

The surface antigen of HBV is produced by culture of genetically-engineered yeast cells which carry the gene coding for major surface antigen of HBV. The HBS Ag is expressed in yeast cells and purified by Himax-technology.

viii) Combined Vaccines

One combined vaccine of the present invention contains inactivated rota strain of 116E and inactivated sabin strain of polio virus. Another combined vaccine of present invention containing inactivated rota strain of 116E, inactivated sabin strain of polio virus type I, II, & III, *Bordetella pertussis* protective antigen (pertactine, pertussis toxoid, filamenteous haemagglutin), Hepatitis B surface antigen, *Haemphilius influenza* type b PRP conjugate antigen, diphtheria toxoid and tetanus toxoid. Therefore combined vaccine of the present invention may also prepared by mixing inactivated rotavirus and sabin strain of polio virus together with diphtheria toxoid, tetanus toxoid, pertussis, *Heamophilis influenzae* type b PRP-TT conjugate antigen and Hepatitis B Surface antigen.

EXAMPLES

The following examples are used to further illustrate the present invention and advantageous thereof. The following specific examples are given with the understanding that those are intended to be illustration without serving as a limitation on the scope of the present invention.

Example 1

Inactivation of Rotavirus

In the present invention live rotavirus was subjected to thermal inactivation at three different temperatures with and/or without a stabilizer sorbitol during inactivation process.

Virus Inactivation Kinetic Study: During the inactivation process, sample of viral harvest was taken and residual live virus particle was tested by immuneperoxidase test.

TABLE 1

| Temp. | 10% sorbitol | Virus sampling time during inactivation kinetic study | | | | | |
|---|---|---|---|---|---|---|---|
| | | $1^{st}$ hr | $2^{nd}$ hr | $3^{rd}$ hr | $4^{th}$ hr | $5^{th}$ hr | $6^{th}$ hr |
| 56° C. | With sugar | ++ | ++ | ++ | ++ | -- | -- |
|  | Without sugar | ++ | ++ | ++ | ++ | -- | -- |
| 60° C. | With sugar | ++ | -- | -- | -- | -- | -- |
|  | Without sugar | ++ | -- | -- | -- | -- | -- |
| 70° C. | With sugar | -- | -- | -- | -- | -- | -- |
|  | Without sugar | -- | -- | -- | -- | -- | -- |

++: indicates presence of residual virus particle at particular point of sampling by immuneperoxidase test
--: indicates absence of residual virus particle by at particular point of sampling by immuneperoxidase test.

Example 2

Concentration and Purification of Inactivated Rotavirus Particle

Inactivated rotavirus harvest was subjected to ultra-filtration using tangential flow filtration. The molecular cut-off cassettes used to remove lower molecular weight impurities are 100 kDa or 300 kDa cassettes. The virus fluid pass through the cassette for several times using TFF system until the desired concentration was obtained. During ultrafiltration process the harvest volume will be made up by phosphate buffer (10-20 mM) or phosphate buffer (10 mM) with 100 mM-136 mM sodium chloride. The pH of buffer will be neutral, preferably the pH will be 7.2±0.2.

Concentrated viral harvest was further purified by ion-exchange chromatography followed by gel permeation chromatography. The concentrate retentate virus material was passed through weak anion exchange chromatography. The chromatography media was equilibrated with 25 or 50 or 100 mM sodium chloride solution containing 10 mM phosphate buffer. The pH of the equilibration buffer solution varies from 7.0 to 7.4. After equilibration, concentrated rotavirus material was passed through weak anion media at the linear flow rate of 45 to 60 cm2/hr. Preferably 60 cm2/hr. The buffer was washed containing 10 mM sodium chloride containing 10 mM phosphate buffer pH at 7.0 to 7.2 was passed at the linear flow rate of 50 cm$^2$/hr to elute the lower molecular weight impurities.

By means of salt gradient bounded rotavirus was eluted and the fraction were pooled with higher OD value at 280 nm. The pooled fractions was dialyzed using 100 kDa or 10 kDa cassettes against 140 mM sodium chloride with 10 mM phosphate buffer at pH 7.0 to 7.4.

The purity and protein composition of inactivated rotavirus particle was determined by SDS-PAGE and western blotting analysis. The protein concentration of purified bulk was quantified by lowrys method.

Example 3

Inactivation of Polio Virus

Inactivation of the poliovirus may be carried out by a commonly employed method. Specifically, the poliovirus may be inactivated by adding an chemical inactivating agent to the live polio virus fluid and thereby fixation of surface protein of the virus. The inactivating agent is preferably formalin. Formalin is used as inactivating agent, the amount of addition is preferably from about 0.001 to about 0.1 w/v % more preferably from about 0.05 w/v % and most preferably about 0.04 w/v %. The content of D antigen unit was calculated after inactivation process in the purified bulk sample treated with or without glycine during inactivation process. The inactivation temperature is most preferably about 37° C. The inactivation period is preferably from about 7 days to 14 days.

TABLE 2

D antigen content in the purified bulk prepared from the viral harvest treated with or without glycine during inactivation process.

| Polio virus | Inactivating agent with concentration | Temperature | Stabilizer used during inactivation process | D-antigen content in the purified bulk |
|---|---|---|---|---|
| Type I | Formalin (0.025%) | 37 C. | With 0.5% glycine | 118 |
| | | | No stabilizer | 82 |
| Type II | Formalin (0.025%) | 37 C. | With 0.5% glycine | 52 |
| | | | No stabilizer | 31 |
| Type III | Formalin (0.025%) | 37 C. | With 0.5% glycine | 128 |
| | | | No stabilizer | 84 |

TABLE 3

Polio virus inactivation kinectic study

| Virus type | Temperature | Residual live virus particle 0 day | $1^{st}$ day | $2^{nd}$ day | $3^{rd}$ day | $4^{th}$ day | $5^{th}$ day | $6^{th}$ day | $7^{th}$ day | $8^{th}$ day | $9^{th}$ day |
|---|---|---|---|---|---|---|---|---|---|---|---|
| Type I | 25 | +++ | +++ | +++ | +++ | +++ | +++ | +++ | +++ | −−− | −−−− |
| | 37 | +++ | +++ | +++ | +++ | +++ | −−−−− | −−−− | −−−− | −−−− | −−−− |
| Type II | 25 | +++ | +++ | +++ | +++ | +++ | +++ | ++++ | +++ | +++ | −−−− |
| | 37 | +++ | +++ | +++ | +++ | +++ | +++ | −−−− | −−−− | −−−− | −−−− |
| TypeIII | 25 | +++ | +++ | +++ | +++ | +++ | +++ | ++++ | +++ | −−−− | −−−− |
| | 37 | +++ | +++ | +++ | +++ | +++ | +++ | −−−− | −−−− | −−−− | −−−− |

++: indicates presence of residual virus particle at particular point of sampling by $CCID_{50}$ −−: indicates absence of residual virus particle by at particular point of sampling by $CCID_{50}$

Example 4

Sabin Polio Virus Concentration and Purification

Individual sabin strain of polio virus type I, type II and type III was purified separately without any cross contamination of virus antigen. Inactivated virus harvest fluid was concentrated to the required volume with an ultrafiltration membrane (sartorius, PESU (polyethersulphone) 100 Kda, 0.7 $m^2$. The concentrated harvest was diafiltered against the phosphate buffer saline to remove lower molecular weight impurities and to reduce sodium chloride concentration from 117 mM to 25 mM. After concentration step in 100 KDa cassette, the cassette has to be washed to remove the virus particle which binded to the membrane cassette. The concentrated virus fluid was further purified with weak anion-exchange chromatography media. Here the weak anion exchange media used as DEAE. The media was packed and equilibrated with 0.1 mol/L of phosphate buffer containing 25 mM sodium chloride. During packing the linear flow rate should be double the rate of sample loading rate. Following the equilibration step concentrated virus fluid was loaded at the linear flow rate of 50 $cm^2$/hr.

The virus particle was eluted with different concentration of sodium chloride ion as per the salt gradient principle. Peak fractions were pooled and dialysed against phosphate buffer. The purified bulk was filtered through 0.2μ PES filter and stored at 2-8 C. Purification of virus fluid of sabin strain type II and type III was carried out in the same way as type I.

Quantification of D-Antigen in Purified Polio Virus Bulk:

The amount of D antigen is measured by an indirect ELISA method using antibodies having a high specificity to the type and the D antigen. The indirect ELISA method begins by coating a microplate with, as the primary antibody, a monoclonal antibody (mouse derived) specific for D antigens of the same type as the antigen to be assayed. The plate was incubated overnight and blocked with 1% BSA. The antigen to be assayed is then diluted and incubated for 1 hr at 37° C. Subsequently type specific rabbit polyclonal antibody of the same type as the antigen to be assayed is placed thereon as the secondary antibody, in addition to which HRPO-labelled anti-rabbit-IgG antibody is placed there, effecting a reaction. Following the reaction, color development is carried out using an O-phenylenediamine solution, and the absorbance at 492 nm is measured absorbance of the assayed antibody and the measured absorbance for a reference antigen by parallel-line Quantative analysis.

Example 5

This example gives the composition and the process of manufacturing of the combination inactivated viral vaccine as per one embodiment of the invention.

A. Composition of the Combination Viral Vaccine as Per the Invention Given in the Below Mentioned Table.

Each 0.5 ml vaccine comprises the following

TABLE 4

| Components | Amount |
|---|---|
| Purified inactivated rotavirus antigen | 5 microgram |
| Inactivated sabin poliovirus (sIPV) | |
| Polio type 1 | 40 D units |
| Polio type 2 | 08 D units |
| Polio type 3 | 32 D units |
| Other Excipients | |
| Aluminium content | 0.25-0.30 mg of $Al^{+3}$ (as aluminium Phosphate) |
| 2-phenoxyethanol | 2.5 mg |
| Phosphate buffer saline | q.s. |

B. The Process of Manufacturing of Combination Viral Vaccine as Per the Invention is Described Below.

1. Formulation Procedure for Component 1:

1.5% Aluminium phosphate gel added to the vessel followed by phosphate buffer saline and the contents was mixed. The mixture was checked and adjusted to fall in a range of pH 6.5-7.00. Component 1 was added to the mixture and stifling the contents for adsorption of viral antigen to the aluminium ions. Further required volume of phosphate buffer saline and 2-phenoxyethanol were mixed to the mixture in the above.

2. Addition of sIPV Bulk:

The contents of the component 1 were mixed with the IPV antigen preparation under stirring to obtain a combination bivalent viral vaccine. Finally the pH was checked and adjust the pH to fall in a range of 6.5 to 7.2.

Example 6

This Example gives a brief on the potency testing carried out for inactivated rota virus antigen and inactivated polio virus antigen and the stability data.

A. Potency Testing Carried Out for Inactivated Rotavirus Antigen and Inactivated Polio Virus Antigen.

| 1. Potency test for Rota vaccine: | |
|---|---|
| Animal species required | Mice. |
| No. of animals required per batch | 20 |
| Route of vaccine administration | subcutaneous |
| Volume of injection | 0.5 ml |
| No. of days animals are housed | 21 days |

Subcutaneous injection of rota vaccine in swiss albino mice: They were pre-bleed and tested for rotavirus specific antibody in test and control group. Mice in each groups of ten were immunized subcutaneously twice with 5 microgram on $0^{th}$ day and $14^{th}$ day. For control mice in group of 10 were injected with placebo on day 0 and $14^{th}$ day. The animals were bled on $21^{th}$ day (post immunization bleeding). Before starting the immunization animals were checked to ensure that weight of the individual mice should not vary by more than 20% from the group mean. An inoculum of 0.5 ml rota vaccine containing 5 μg of antigen with other excipients was used per dose.

Serum was separated from the immunized group and control group. Neutralizing antibody titres agaiint the rota virus vaccine were measured by Serum Neutralization test. 100 Floruscent focus unit of the 116 E rota virus strain was used as to neutralize the 2 fold diluted sera and tested in Ma104 cell line. Serially diluted the sera at 2 fold dilution, and mixed the diluted antibody with activated rotavirus. Incubate the antigen-antibody mixture at 37° C. for 1 hr. After incubation the Ag-Ab mixture was added to Ma104 monolayer cell sheet in multiwell plate. Incubated the plate for 1 hr at 37° C. for virus adsorption. In next step added 100 μl of EMEM containing 10% FBS was added to each well and incubate the plate at 37 C for 24 hrs. After fixing with formalin, wash the plate with PBS and then infected cells were stained with monoclonal antibody diluted at 1:1000 directed against rota virus 116 E VP6 structural protein for 1 hr at 37 C. A hydrogen peroxide labeled goat-anti-mouse diluted at 1:1000 was used as conjugate and OPD in 0.05 sodium acetate buffer containing 0.01% hydrogen peroxide was used as substrate. The neutralizing antibody titre were defined as the reciprocal of the serum dilution showing 50% reduction in the number of infected cells.

| 2. Potency test of polio vaccine(type I, type II and type III) | |
|---|---|
| Animal species required | Rat |
| No. of animals required per batch | 80 |
| Route of vaccine administration | Intramuscular |
| Volume of injection | 0.5 ml |
| No. of days animals are housed | 21 days |

Test vaccine and reference vaccine was injected intramuscularly into the hindlimbs of rat of four dilutions (2 fold) of the vaccine to be examined. 21 days following injection, blood was drawn individually from each animal and the serum was separated, then complement was inactivated by heating at 56° C. for 30 minutes in temperature controlled water-bath. Serum for each animal of the test vaccine group and reference vaccine group were placed in at least three wells for each serum, and 2-fold serially diluted with EMEM medium. To the serially diluted sera added 100 CCID50 of polio virus to each well and incubated for 3 hr at 37° C. for antigen-antibody reaction in the presence of 5% CO2. After incubation 10000 cells was added to each well and it was incubated for 5 days. After completion of culturing, the CPE (cytopathic effect) for each well were examined, the sera dilution ratio at the time of 50% neutralization was calculated and the reciprocal of the dilution factor was calculated as neutralization antibody titre.

B. Stability Study of Inactivated Polio Virus Vaccine and Inactivated Rota Virus Vaccine:

The tests were carried out as given in the above table. The combined viral vaccine was measured by carrying out an test at 5±3° C. vaccine storage. The stability was evaluated by potency tests on each of the virus.

TABLE 5

I. Combination vaccine-long term stability study (5 ± 3° C.) of sabin strain polio vaccine (Type I, II and III) and inactivated rota virus vaccine for period of 12 months.

| | | | Potency value of combination IPV-IRV vaccine | | | | | | |
|---|---|---|---|---|---|---|---|---|---|
| Antigen | Antigen concentration | Potency Specification | 0 day | $1^{st}$ month | $2^{nd}$ month | $3^{rd}$ month | $6^{th}$ month | $9^{th}$ month | $12^{th}$ month |
| polio type $1^a$ | 40 D unit | Relative potency equal or higher than Reference vaccine | 1.5 | 1.4 | 1.15 | 1.3 | 1.2 | 1.3 | 1.4 |
| polio type $2^a$ | 8 D unit | | | | | | | | |
| polio type $3^a$ | 32 D unit | | | | | | | | |
| Inactivated rota vaccine (5 μg/ml)$^b$ | 5 μg of purified Antigen | Neutralizing antibody titer | 1144 | 1120 | 998 | 1056 | 1114 | 1072 | 978 |

$^a$For inactivated polio vaccine, the potency value of the test vaccine was compared with reference vaccine by relative unit. For example if the relative potency value of reference vaccine was 1, test vaccine relative potency value will be lessthan 1 or morethan 1.
$^b$For inactivated rota virus vaccine potency value was based on the neutralizing antibody titer.

TABLE 6

II. Long term stability (5 ± 3° C.) of individual component inactivated rota vaccine.

| | | | Relative Potency value of IPV vaccine | | | | | | |
|---|---|---|---|---|---|---|---|---|---|
| Antigen | Antigen concentration | Potency Specification | 0 day | $1^{st}$ month | $2^{nd}$ month | $3^{rd}$ month | $6^{th}$ month | $9^{th}$ month | $12^{th}$ month |
| polio type 1 | 40 D unit | Relative potency equal or higher than Reference vaccine | 1.25 | 1.12 | 1.4 | 1.45 | 1.3 | 1.2 | 1.15 |
| polio type 2 | 8 D unit | | | | | | | | |
| polio type 3 | 32 D unit | | | | | | | | |

TABLE 7

III. Real time stability (5 ± 3° C.) of individual component Polio vaccine (Type I, II and III)

| | | | Potency value of IRV vaccine (Neutralizing antibody titer) | | | | | | |
|---|---|---|---|---|---|---|---|---|---|
| Antigen | Antigen concentration | Potency Specification | 0 day | $1^{st}$ month | $2^{nd}$ month | $3^{rd}$ month | $6^{th}$ month | $9^{th}$ month | $12^{th}$ month |
| Inactivated rota vaccine (5 μg/ml) | 5 μg of purified Antigen | Neutralizing antibody titer | 1256 | 1020 | 1114 | 986 | 1230 | 1096 | 1218 |

Example 7

This example given the composition and the process of manufacturing of the heptavalent vaccine as per one of the aspect of invention.
A. Composition of Heptavalent Vaccine as Per the Invention is as Under—Each 0.5 ml of vaccine comprise the following

TABLE 8

| Components | Amount |
|---|---|
| Dipthreia Toxoid[1](DT) | 25 LF adsorbed |
| Tetanus Toxoid[1](DT) | 7.5 LF adsorbed |
| Acellular pertussis[1](aP) | Pertussus Toxoid(PT) adsorbed 25 μg |
| Filamentous Hemagglutinin (FHA) adsorbed | 25 μg |
| Hepatitis B surface antigen[1](HBsAg) | 10 μg adsorbed |
| *Haemophilius influenza*(Hib)b | 10 μg capsular polysaccharide antigen |
| Inactivated rota virus antigen[2](IRV) | 5 μg adsorbed |
| Inactivated Poliovirus(IPV) | |
| Polio type 1 | 40 D units |
| Polio type 2 | 08 D units |
| Polio type 3 | 32 D units |

TABLE 8-continued

| Other Excipients | Amount |
|---|---|
| Aluminium content | 0.50-0.60 mg of Al$^{+3}$ (as aluminium Phosphate) 0.25-0.30 mg of Al$^{+3}$ (as aluminium Hydroxide) |
| 2-phenoxyethanol | 2.5 mg |
| Phosphate buffer saline | q.s. |

$^1$on a aluminium phosphate
$^2$on a aluminium hydroxide
q.s. Quantity sufficient.

B. The Process of Manufacturing of Heptavalent Vaccine as Per the Invention is as Under:

1. Formulation Procedure for Component I

Required amount of 1.5% of Aluminium phosphate gel are added into the vessel at the concentration each 0.5 ml of final vaccine should contain of 0.50-0.60 mg of Al$^{+3}$ as aluminium phosphate. Required amount of phosphate buffer saline pH 7.2±0.4 was added to the aluminium phosphate gel. The contents was checked and adjust the pH in such a way that it should fall in a range of pH 6.0-6.5. Following the above step diptheria toxoid was added in such way that the final vaccine formulation should have 25 LF (Limits of flocculation) per 0.5 ml. Next antigen tetanus toxoid was added at the concentration in the final formulation each 0.5 ml of vaccine should contain 7.5 LF (Limits of flocculation). Acellular pertussis components like pertussis toxoid and filamenteous hemagglutinin was added to the above mixture at 25 µg of each component in 0.5 ml. Finally Hepatitis B surface antigen was added to the above mixture at appropriate concentration. The above contents were mixed, the pH was adjusted to fall in the range of 6.0 to 7.0. Further, phosphate buffer saline was added, the pH was checked and adjusted to fall in a range of pH: 6.5 to 7.2.

2. Formulation Procedure for Component II.

2.1% Aluminium hydroxide gel was taken in a vessel and phosphate buffer saline was added. The above contents were mixed, the pH was adjusted to fall in the range of 7.0 to 7.4. The inactivated rota virus antigen was added in such a way that each 0.5 ml of final vaccine should contain 5 µg of viral antigen. Further phosphate buffer saline was added, the pH was checked and adjusted to fall in a range of pH: 6.5 to 7.2.

3. Mixing of Component I and Component II.

This step was carried out by transferring the content of the component II to the component I to obtain a mixture.

4. Addition of Hib Type b and IPV Bulk:

The above mixture comprising the components I and II were mixed with Hib antigen. The content were mixed under stirring to obtain a Heptavalent vaccine. Further 2-phenoxyethanol were transferred to a vessel and phosphate buffer saline was added to make up the volume to the required amount. The pH was checked and adjusted to fall in a range of 6.5 to 7.2.

Example 8

This example gives a brief on the in-vivo potency testing carried out for diptheria, tetanus, pertussis, Hepatitis B, *haemophilius influenza* Type b, rotavirus antigen and polio virus antigen and the stability data.

A. Potency Testing Carried Out for Diptheria, Tetanus, Pertussis, Hepatitis B, *Haemophilius Influenza* Type b, Rota Virus Antigen and Polio Virus Antigen (IPV-IRV-DTaP-rHBsAg-Hib Antigen).

| a. Potency test for IPV. | |
|---|---|
| Animal species required | Rat |
| No. of animals required per batch | 80 |
| Route of vaccine administration | Intramuscular |
| Volume of injection | 0.5 ml |
| No. of days animals are housed | 21 days |

Test vaccine and reference vaccine was injected intramuscularly into the hindlimbs of rat of four dilutions (2 fold) of the vaccine to be examined. 21 days following injection, blood was drawn individually from each animal and the serum was separated, then complement was inactivated by heating at 56° C. for 30 minutes in temperature controlled water-bath. Serum for each animal of the test vaccine group and reference vaccine group are placed in at least three wells for each serum, and 2-fold serially diluted with EMEM medium. To the serially diluted sera add 100 CCID50 of polio virus to each well and incubated for 3 hr at 37° C. for antigen-antibody reaction in the presence of 5% CO2. After incubation 10000 cells was added to each well and it was incubated for 5 days. After completion of culturing, the CPE (cytopathic effect) for each well are examined, the sera dilution ratio at the time of 50% neutralization is calculated and the reciprocal of the dilution factor was calculated as neutralization antibody titre.

| b. Potency test for IRV. | |
|---|---|
| Animal species required | Mice. |
| No. of animals required per batch | 20 |
| Route of vaccine administration | subcutaneous |
| Volume of injection | 0.5 ml |
| No. of days animals are housed | 21 days |

Subcutaneous injection of rota vaccine in swiss albino mice. They were pre-bleed and tested for rotavirus specific antibody in test and control group. Mice in each groups of ten were immunized subcutaneously twice with 5 microgram on 0$^{th}$ day and 14$^{th}$ day. For control mice in group of 10 were injected with placebo on day 0 and 14$^{th}$ day. The animals were bled on 21$^{th}$ day (post immunization bleeding). Before starting the immunization animals were checked to ensure that weight of the individual mice should not vary by more than 20% from the group mean. An inoculum of 0.5 ml rota vaccine containing 5 µg of antigen with other excipients is used per dose.

Serum was separated from the immunized group and control group. Neutralizing antibody titres against the rotavirus vaccine were measured by Serum Neutralization test. 100 Floruscent focus unit of the 116 E rotavirus strain was used as to neutralize the 2 fold diluted sera and tested in Ma104 cell line. Serially dilute the sera at 2 fold dilution and mix the diluted antibody with activated rotavirus. Incubate the antigen-antibody mixture at 37° C. for 1 hr. After incubation the Ag-Ab mixture was added to Ma104 monolayer cell sheet in multiwell plate. Incubate the plate for 1 hr at 37° C. for virus adsorption. In next step added 100 µl of EMEM containing 10% FBS was added to each well and incubate the plate at 37 C for 24 hrs. After fixing with formalin, wash the plate with PBS and then infected cells were stained with monoclonal antibody diluted at 1:1000 directed against rota virus 116 E VP6 structural protein for 1 hr at 37 C. A hydrogen peroxide labeled goat-anti-mouse diluted at 1:1000 was used as conjugate and OPD in 0.05 sodium acetate buffer containing 0.01% hydrogen peroxide was used as substrate. The neutralizing antibody titre were defined as the reciprocal of the serum dilution showing 50% reduction in the number of infected cells.

c. Potency test for pertussis protective antigen:

| | |
|---|---|
| Animal species required | Mice |
| No. of animals required per batch | 116 |
| Route of vaccine administration | Intramuscular |
| Volume of injection | 0.5 ml |
| No. of days animals are housed | 28 days |

The test vaccine and the reference vaccine are diluted in 2 fold in three different dilutions of the vaccine to be tested in mice, each dilution injected to a group of mice. The test and reference vaccine injected intraperitonally to each mouse 0.5 ml of the dilution. Bleed the animal after 21 days of vaccination. Sera was separated, complement inactivated and neutralizing antibody was titrated by ELISA.

Microtitre plates are coated with the purified antigen at a concentration of 100 ng of protective antigen per well. After washing unreacted sites are blocked by BSA and then washed. After incubation at 37° C. for 1 hr, the plates are washed, anti-mouse IgG conjugate was added to each well and incubated for 1 hr at 37 C. After washing a substrate is added from which the bound enzyme conjugate liberates a color it was quantified by the measurement of absorbance. Based upon the absorbance values the antibody titres in the sera of mice immunized with reference and the test vaccines are calculated and from the values the potency of the test vaccine in relation to the reference vaccine was calculated.

d. Potency test for diptheria toxoid:

| | |
|---|---|
| Animal species required | Guinea pig |
| No. of animals required per batch | 125 |
| Route of vaccine administration | subcutaneous |
| Volume of injection | 0.5 ml |
| No. of days animals are housed | 33 days |

The test vaccine, standard vaccine and toxin are required for the assay. Dilution of the test vaccine and the standard vaccine is carried out with 0.9% saline and dilution of the toxin solution is carried out with a 10 mM phosphate buffer containing 137 mM of sodium chloride. The test vaccine and the standard vaccine are serial diluted at in 2 fold (three different dilution in test and reference vaccine). Using one group of at least 20 guinea pig for each dilution of the test vaccine and the reference, each animal is given a single subcutaneous injection of 0.5 ml. In the middle of the $4^{th}$-$5^{th}$ week challenge the test, reference and control group with diptheria toxin containing 100 LD50. Twice a day for 5 days observe the guinea pigs and record the number of guinea pig protected by each dilution of test vaccine and reference vaccine. Potency was estimated by comparing the values between the test and reference by probit method.

e. Potency tesy for Tetanus toxoid:

| | |
|---|---|
| Animal species required | mice |
| No. of animals required per batch | 125 |
| Route of vaccine administration | subcutaneous |
| Volume of injection | 0.5 ml |
| No. of days animals are housed | 29 days |

The test vaccine, standard vaccine and toxin are required. Dilution of the test vaccine and the reference vaccine is carried out with 0.9% saline, dilution of the toxin solution is carried out with a 10 mM phosphate buffer containing 137 mM of sodium chloride. The test vaccine and the reference are diluted serially in 4 fold. Using one group of at least twenty 17-20 gm weighed mice for each dilution of the test vaccine and the reference vaccine, each animal is given a single subcutaneous injection of 0.5 ml. After 21 days following immunization each mouse is challenged with about 100 LD50 of toxin and observed for 7 days. The potecy was calculated by statistical method by comparing the test and control vaccine.

f. Potency test for Hepatitis B surface antigen:

| | |
|---|---|
| Animal species required | Mice |
| No. of animals required per batch | 180 |
| Route of vaccine administration | Intra-peritoneally |
| Volume of injection | 1 ml |
| No. of days animals are housed | 28 days |

The potency of the test vaccine compared with standard vaccine by determining the specific anti-HBsAg antibodies in mice. Inject intra-peritoneally into mice weighing between 15 to 20 gms at four dilution (4 fold) of the test vaccine and standard vaccine. One group of control animals remain unvaccinated but is injected intra-peritoneally with the same volume of the diluent alone. Bleed the animal at $28^{th}$ day of post vaccination and sera was separated. Assay the individual sera for specific HBsAg antibody concentration by ELISA method. The results of test were analyzed by standard statistical method. The percentage of animals showing seroconversion in each group is transformed and a parallel line model using the log dose response curve. The potency of the test vaccine was compared relative to the reference preparation.

g. Potency test for *Haemophilius influenza* type b PRP conjugate vaccine:

| | |
|---|---|
| Animal species required | Mice |
| No. of animals required per batch | 16 |
| Route of vaccine administration | Intra-peritoneally |
| Volume of injection | 0.5 ml |
| No. of days animals are housed | 21 days |

This method is to quantitate the antibodies induced in mice by the test vaccine by mice immunogenicity assay. Immunization of Mice is done by taking single dilutions of 4-fold of the Human dose are prepared in sterile saline. Two dose of 4 fold dilution of vaccine was injected intra-peritoneally with 0.5 mL (8 mice each weighing 15 to 20 gms) on $0^{th}$ day and $14^{th}$ day. One Control group of 8 mice each are inoculated intra-peritoneally with 0.5 mL of Sterile Saline on Oh day and $14^{th}$ day.

Bleed the test group and control group on 21$^{st}$ day and separated the serum for antibody titer. The test is carried by ELISA method to determine the number of fold antibody titre rise. The antibody titer should not be less than 4 fold increase in antibody titre in vaccinated group compared to control group.

B. Stability of IPV-IRV-Hib-HBsAg-DaPT:

The combined vaccine was measured by carrying out an test at 5±3° C. vaccine storage. The stability was evaluated by potency tests on each of the virus, sub-unit bacterial vaccine and recombinant vaccine.

TABLE 9

I. Combination vaccine long term stability(5 ± 3° C.) of IPV-IRV-Hib-HBsAg-DaPT.

| Antigen | Antigen concentration | Potency Specification | Potency value of IPV-IRV-Hib-HBsAg-DaPT vaccine | | | | | | |
|---|---|---|---|---|---|---|---|---|---|
| | | | 0 day | 1$^{st}$ month | 2$^{nd}$ month | 3$^{rd}$ month | 6$^{th}$ month | 9$^{th}$ month | 12$^{th}$ month |
| polio type 1$^a$ polio type 2$^a$ polio type 3$^a$ | 40 D unit 8 D unit 32 D unit | Relative potency equal or higher than Reference vaccine | 1.4 | 1.12 | 1.15 | 1.3 | 1.25 | 1.4 | 1.2 |
| Inactivated rota vaccine$^b$ | 5 μg of purified Antigen | Neutralizing antibody titer | 1124 | 1020 | 956 | 1114 | 1056 | 1006 | 1078 |
| Diptheria toxoid adsorbed$^c$ | 25 LF | NLT 30 units per dose compared to reference vaccine | 52 | 48 | 51 | 47 | 44 | 46 | 43 |
| Tetanus toxoid$^c$ | 7.5 LF | NLT 60 units per dose compared to reference vaccine | 85 | 87 | 89 | 84 | 79 | 75 | 81 |
| Pertussis toxoid Filamentous haemagglutin$^a$ | 25 μg each | Relative potency equal or higher than Reference vaccine | 1.5 | 1.4 | 1.5 | 1.2 | 1.4 | 1.15 | 1.6 |
| Hib type b PRP-T conjugate antigen$^d$ | 10 μg | Not less than 4 fold increase in antibody titre in vaccinated group compared to control group | 8.8 | 9.0 | 8.5 | 8.2 | 7.5 | 7.7 | 7.4 |
| Hepatitis B surface antigen$^a$ | 10 μg | Relative potency equal or higher than Reference vaccine | 1.7 | 1.9 | 1.45 | 1.6 | 1.40 | 1.6 | 1.5 |

$^a$For inactivated polio vaccine, acellular pertussis vaccine and Hepatitis vaccine the potency value of the test vaccine was compared with reference vaccine by relative unit. For example if the relative potency value of reference vaccine was 1, test vaccine relative potency value will be less than 1 or more than 1.
$^b$For inactivated rota virus vaccine potency value was based on the neutralizing antibody titer.
$^c$For Diptheria and Tetanus toxoid vaccine potency value depend on the comparison of units obtained from the reference vaccine by ED$_{50}$.
$^d$For Hib type b PRP-T conjugate antigen, potency value depends upon number of fold increase in antibody in vaccinated group compared to unvaccinated group.

TABLE 10

II. Long term stability (5 ± 3° C.) of combination DapT vaccine

| Antigen | Antigen concentration | Potency Specification | Potency value of DapT vaccine | | | | | | |
|---|---|---|---|---|---|---|---|---|---|
| | | | 0 day | 1$^{st}$ month | 2$^{nd}$ month | 3$^{rd}$ month | 6$^{th}$ month | 9$^{th}$ month | 12$^{th}$ month |
| Diptheria toxoid adsorbed | 25 LF | NLT 30units per dose compared to reference vaccine | 55 | 52 | 48 | 46 | 52 | 56 | 51 |
| Tetanus toxoid | 7.5 LF | NLT 60units per dose compared to reference vaccine | 85 | 79 | 90 | 78 | 85 | 84 | 82 |
| Pertussis toxoid Filamentous haemagglutin | 25 μg each | Relative potency equal or higher than Reference vaccine | 1.2 | 1.12 | 1.3 | 1.4 | 1.5 | 1.3 | 1.12 |

TABLE 11

1. Long term stability (5 ± 3° C.) of individual component Hib vaccine

| | | | Potency value of Hib vaccine | | | | | | |
|---|---|---|---|---|---|---|---|---|---|
| Antigen | Antigen concentration | Potency Specification | 0 day | 1st month | 2nd month | 3rd month | 6th month | 9th month | 12th month |
| Hib type b PRP-TT conjugate antigen | 10 µg | Not less than 4 fold increase in antibody titre in vaccinated group compared to control group | 8.5 | 8.8 | 7.5 | 7.2 | 7.9 | 8.2 | 7.4 |

TABLE 12

2. Long term stability (5 ± 3° C.) of individual component rHBsAg vaccine

| | | | Potency value of rHBsAg vaccine | | | | | | |
|---|---|---|---|---|---|---|---|---|---|
| Antigen | Antigen concentration | Potency Specification | 0 day | 1st month | 2nd month | 3rd month | 6th month | 9th month | 12th month |
| Hepatitis B surface antigen | 10 µg | Relative potency equal or higher than Reference vaccine | 1.4 | 1.12 | 1.4 | 1.5 | 1.15 | 1.2 | 1.4 |

Thus, it can seen that the potency value of the Heptavalent vaccine equal or superior than individual component vaccine which was tested and also vaccine was stable for more than one year.

We claim:

1. A stable heptavalent combination composition consisting of:
   a) inactivated rotavirus strain 116E;
   b) inactivated sabin poliovirus types I, II, and III;
   c) acellular *bordatella pertussis* antigen;
   d) hepatitis B surface antigen (HBsAg);
   e) *haemophilus influenza* type b (Hib) antigen conjugated to a carrier protein;
   f) diptheria toxoid (DT);
   g) tetanus toxoid (TT); and
   h) one or more excipients;
   wherein any of the each component abovementioned individual antigens is not impaired by the presence of other component antigens;
   wherein the potency value of the heptavalent combination composition is equal or superior than individual component composition; and
   wherein the heptavalent combination composition remains stable for at least one year.

2. The composition according to claim 1, wherein the inactivated rotavirus antigen, the acellular *bordatella pertussis* antigen, the hepatitis B surface antigen (HBsAg), the *haemophilus influenza* type b (Hib) conjugate antigen, the diptheria toxoid antigen (DT), and the tetanus toxoid antigen (TT) are all adsorbed to an adjuvant selected from aluminium phosphate or aluminium hydroxide.

3. The composition according to claim 1, wherein the inactivated rotavirus strain 116E consists of an antigenic makeup selected from P[10]G9 and P[11]G10.

4. The composition according to claim 1, wherein the inactivated sabin poliovirus types I, II, and III consists of D and C antigens of sabin poliovirus types I, II, and III.

5. The composition according to claim 1, wherein the inactivated sabin poliovirus types I, II, and III consists of D antigens of sabin poliovirus types I, II, and III.

6. The composition according to claim 1, wherein the acellular *bordatella pertussis* antigen consists of one or more antigens selected from the group consisting of filamentous hemagglutinin (FHA), pertussis toxoid (PT), and pertactin (P69 or PRN).

7. The composition according to claim 1, wherein the acellular *bordatella pertussis* antigen consists of filamentous hemagglutinin (FHA) and pertactin (P69 or PRN).

8. The composition according to claim 1, wherein the acellular *bordatella pertussis* antigen consists of pertussis toxoid (PT) and pertactin (P69 or PRN).

9. The composition according to claim 1, wherein the *haemophilus influenza* type b (Hib) antigen is capsular polysaccharide polyribosylribitol phosphate (PRP).

10. The composition according to claim 1, wherein the *haemophilus influenza* type b (Hib) antigen is capsular polysaccharide polyribosylribitol phosphate (PRP) and the carrier protein is tetanus toxoid (tt).

11. The composition according to claim 1, wherein
   (a) the inactivated rotavirus antigen (IRV) is present in an amount 2.5 µg to 15 µg per 0.5 ml;
   (b) antigen D of the sabin inactivated polio virus strains type-I, type-II and type-III is present in a ratio of 40:8:32 units per 0.5 ml;
   (c) the acellular *bordatella pertussis* antigen consists of filamentous hemagglutinin (FHA) and pertactin (P69 or PRN), wherein FHA is present in an amount of 5 µg to 30 µg per 0.5 ml, and pertactin is present in an amount of 8 µg to 10 µg per 0.5 ml;
   (d) the hepatitis B surface antigen (HBsAg) is present in an amount of 5 µg to 15 µg per 0.5 ml;
   (e) the *haemophilus influenza* type b (Hib) antigen is capsular polysaccharide polyribosylribitol phosphate (PRP) and the carrier protein is tetanus toxoid (tt), wherein the PRP-tt conjugate is present in an amount of 8 µg to 15 µg per 0.5 ml;

(f) the diptheria toxoid (DT) is present in an amount of 15 LF to 30 LF per 0.5 ml; and (g) the tetanus toxoid (TT) is present in an amount of 5 LF to 15 LF per 0.5 ml.

12. The composition according to claim 1, wherein (a) the inactivated rotavirus antigen (IRV) is present in an amount 2.5 µg to 15 µg per 0. 5 ml;

(b) antigen D of the sabin inactivated polio virus strains type-I, type-II and type-III is present in a ratio of 40:8:32 units per 0.5 ml;

(c) the acellular *bordatella pertussis* antigen consists of pertussis toxoid (PT) and pertactin (P69 or PRN), wherein PT is present in an amount of 5 µg to 30 µg per 0.5 ml, and pertactin is present in an amount of 8 µg to 10 µg per 0.5ml;

(d) the hepatitis B surface antigen (HBsAg) is present in an amount of 5 µg to 15 µg per 0.5 ml;

(e) the *haemophilus influenza* type b (Hib) antigen is capsular polysaccharide polyribosylribitol phosphate (PRP) and the carrier protein is tetanus toxoid (tt), wherein the PRP-tt conjugate is present in an amount of 8 µg to 15 µg per 0.5 m;

(f) the diptheria toxoid (DT) is present in an amount of 15 LF to 30 LF per 0.5 ml; and (g) the tetanus toxoid (TT) is present in an amount of 5 LF to 15 LF per 0.5 ml.

13. A stable heptavalent combination composition consisting of:

a) inactivated rotavirus strain 116E, wherein the rotavirus comprises an antigenic makeup selected from P[10]G9 and P[11]G10;

b) D antigens of inactivated sabin poliovirus types I, II, and II;

c) at least one acellular *bordatella pertussis* antigen selected from the group of antigens consisting of filamentous hemagglutinin (FHA), pertussis toxoid (PT), and pertactin (P69 or PRN);

d) hepatitis B surface antigen (HBsAg);

e) *haemophilus influenza* type b (Hib) antigen conjugated to a carrier protein, wherein the *haemophilus influenza* type b (Hib) antigen is capsular polysaccharide polyribosylribitol phosphate (PRP) and the carrier protein is tetanus toxoid (tt);

f) diptheria toxoid (DT);

g) tetanus toxoid (TT); and h) one or more excipients;

wherein any of the each component abovementioned individual antigens is not impaired by the presence of other component antigens;

wherein the potency value of the heptavalent combination composition is equal or superior than individual component composition; and wherein the heptavalent combination composition remains stable for at least one year.

14. The composition according to claim 13, wherein (a) the inactivated rotavirus antigen (IRV) is present in an amount 2.5 µg to 15 µg per 0.5 ml;

(b) the D antigens of the sabin inactivated polio virus strains type-I, type-II and type-III are present in a ratio of 40:8:32 units per 0.5 ml;

(c) the acellular *bordatella pertussis* antigens consists of filamentous hemagglutinin (FHA) and pertactin (P69 or PRN), wherein FHA is present in an amount of 5 µg to 30 µg per 0.5 ml, and pertactin is present in an amount of 8 µg to 10 µg per 0.5 ml;

(d) the hepatitis B surface antigen (HBsAg) is present in an amount of 5 µg to 15 µg per 0.5 ml;

(e) the *haemophilus influenza* type b (Hib) antigen is capsular polysaccharide polyribosylribitol phosphate (PRP) and the carrier protein is tetanus toxoid (tt), wherein the PRP-tt conjugate is present in an amount of 8 µg to 15 µg per 0.5 ml;

(f) the diptheria toxoid (DT) is present in an amount of 15 LF to 30 LF per 0.5 ml; and (g) the tetanus toxoid (TT) is present in an amount of 5 LF to 15 LF per 0.5 ml.

15. The composition according to claim 13, wherein (a) the inactivated rotavirus antigen (IRV) is present in an amount 2.5 µg to 15 µg per 0.5 ml;

(b) the D antigens of the sabin inactivated polio virus strains type-I, type-II and type-III is present in a ratio of 40:8:32 units per 0.5 ml;

(c) the acellular *bordatella pertussis* antigens consists of pertussis toxoid (PT) and pertactin (P69 or PRN), wherein PT is present in an amount of 5 µg to 30 µg per 0.5 ml, and pertactin is present in an amount of 8 µg to 10 µg per 0.5ml;

(d) the hepatitis B surface antigen (HBsAg) is present in an amount of 5 µg to 15 µg per 0.5 ml;

(e) the *haemophilus influenza* type b (Hib) antigen is capsular polysaccharide polyribosylribitol phosphate (PRP) and the carrier protein is tetanus toxoid (tt), wherein the PRP-tt conjugate is present in an amount of 8 µg to 15 µg per 0.5 m;

(f) the diptheria toxoid (DT) is present in an amount of 15 LF to 30 LF per 0.5 ml; and (g) the tetanus toxoid (TT) is present in an amount of 5 LF to 15 LF per 0.5 ml.

\* \* \* \* \*